United States Patent
Adams et al.

(10) Patent No.: US 9,903,839 B2
(45) Date of Patent: Feb. 27, 2018

(54) SYSTEM AND METHOD FOR SUBSEA INSPECTION

(71) Applicant: Oceaneering International, Inc., Houston, TX (US)

(72) Inventors: Mark Alan Adams, Montgomery, TX (US); John Joseph Boyle, Friendswood, TX (US)

(73) Assignee: Oceaneering International, Inc., Houston, TX (US)

( * ) Notice: Subject to any disclaimer, the term of this patent is extended or adjusted under 35 U.S.C. 154(b) by 206 days.

(21) Appl. No.: 14/409,993

(22) PCT Filed: Jun. 21, 2013

(86) PCT No.: PCT/US2013/047084
§ 371 (c)(1),
(2) Date: Dec. 19, 2014

(87) PCT Pub. No.: WO2013/192536
PCT Pub. Date: Dec. 27, 2013

(65) Prior Publication Data
US 2015/0204821 A1    Jul. 23, 2015

Related U.S. Application Data

(60) Provisional application No. 61/662,789, filed on Jun. 21, 2012.

(51) Int. Cl.
*G01N 29/32* (2006.01)
*G01N 29/04* (2006.01)
(Continued)

(52) U.S. Cl.
CPC ....... *G01N 29/2412* (2013.01); *G01N 29/041* (2013.01); *G01N 29/225* (2013.01);
(Continued)

(58) Field of Classification Search
CPC ............. G01N 29/2412; G01N 29/265; G01N 29/041; G01N 29/225; G01N 29/226;
(Continued)

(56) References Cited

U.S. PATENT DOCUMENTS 4,956,868 A * 9/1990 Carlson .................. H04R 11/00
                                                      381/189
5,537,876 A * 7/1996 Davidson ............. G01N 29/041
                                                      228/104

(Continued)

FOREIGN PATENT DOCUMENTS

GB        2475337        5/2011
WO        2004027991    4/2004

OTHER PUBLICATIONS

Patent Examination Report No. 1 for Australian Patent Application No. 2013278060 dated Jul. 17, 2015.
(Continued)

*Primary Examiner* — J M Saint Surin
(74) *Attorney, Agent, or Firm* — Tumey L.L.P.

(57) ABSTRACT

Embodiments include subsea ultrasonic inspection systems employing electromagnetic acoustic transducers (EMATs) to inspect subsea objects, such as subsea tubular items, conduit, piping, pipelines, risers, vessels, structures, and so forth.

18 Claims, 9 Drawing Sheets

(51) Int. Cl.
*G01N 29/22* (2006.01)
*G01N 29/265* (2006.01)
*G01N 29/24* (2006.01)
*B63C 11/52* (2006.01)

(52) U.S. Cl.
CPC ......... *G01N 29/226* (2013.01); *G01N 29/265* (2013.01); *G01N 29/32* (2013.01); *B63C 11/52* (2013.01); *G01N 2291/0422* (2013.01); *G01N 2291/0427* (2013.01); *G01N 2291/2634* (2013.01)

(58) Field of Classification Search
CPC .......... G01N 29/32; G01N 2291/0427; G01N 2291/2634; G01N 2291/0422; B63C 11/52
USPC .......................................................... 73/622
See application file for complete search history.

(56) References Cited

U.S. PATENT DOCUMENTS

| | | | |
|---|---|---|---|
| 5,619,423 A | 4/1997 | Scrantz | |
| 5,729,134 A | 3/1998 | Lavan, Jr. et al. | |
| 6,125,706 A * | 10/2000 | Buttram | B06B 1/045 |
| | | | 73/643 |
| 6,176,132 B1 | 1/2001 | Maclauchlan | |
| 2001/0017541 A1 | 8/2001 | Kwun et al. | |
| 2003/0011275 A1 | 1/2003 | Nasrollahzadeh | |
| 2007/0074572 A1* | 4/2007 | Koch | B06B 1/04 |
| | | | 73/627 |
| 2007/0151344 A1* | 7/2007 | Meethal | G01N 29/2412 |
| | | | 73/649 |
| 2011/0259108 A1* | 10/2011 | Ege | B06B 1/04 |
| | | | 73/643 |
| 2013/0111998 A1* | 5/2013 | Hull | G01N 29/043 |
| | | | 73/643 |

OTHER PUBLICATIONS

Van Den Berg W H et al: "Development of and electromagnetic acoustic transudcer for inspectin the wall thickness of offshore risers from the inside" Ultrasonics, IPC Science and Technology Press Ltd. Guilford, GB, vol. 26, No. 1, pp. 14-22, Jan. 1, 1988.
Ryan Phipps: "Effective subsea inspection", Retrieved from the Internet: URL:http://www.sonomatic.com/publications/effective_ subsea_inspection.pdf Retrieved Apr. 14, 2016 published Apr. 1, 2011.
Wernli R et al. "ROV Technology Update From and International Perspective", OCEANS 1984, IEEE, Piscataway, NJ, USA, pp. 639-645, dated Sep. 1, 1984.
Extended European Search Report for European Application No. 13807739.1-1554/2864773 dated Apr. 26, 2016.
International Search Report and Written Opinion for PCT/US13/47084 dated Jun. 21, 2013.

* cited by examiner

SYSTEM AND METHOD FOR SUBSEA INSPECTION

BACKGROUND

1. Field of the Invention

The present invention relates generally to subsea inspection systems, and more particularly to subsea ultrasonic inspection systems employing electromagnetic acoustic transducers (EMATs) to inspect subsea objects, such as subsea tubular items, conduit, piping, pipelines, risers, vessels, structures, and so forth.

2. Description of the Related Art

This section is intended to introduce the reader to aspects of art that may be related to aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Subsea piping and vessels, and other subsea structures, may be involved in the recovery and transmission of energy resources, such as oil and gas. In a more general and broader sense, such subsea piping and structures may be found in a range of commercial and industrial applications, including utility distribution, manufacturing processes, chemical and petrochemical transport, energy transmission, plumbing, heating and cooling, as well as in the recovery of spent chemicals/compounds, and so forth. In operation, subsea piping, vessels, and structures may serve to collect, distribute, and transport water, steam, chemicals, petrochemicals, crude oil, natural gas, and other liquids, gases, and components. Subsea piping and vessels, and other subsea structures, have played a beneficial role in improving productivity in delivery of resources, including applications in the recovery of offshore oil and gas. Indeed, world economies depend on the capability of subsea pipelines and structures to transport feedstocks and products to a diverse range of customers and end-users. Construction of subsea pipelines and structures has occurred over the last several decades, including many such relatively old subsea pipelines and structures still in use and in service.

Subsea piping, pipeline, vessel, and structural failures may be caused by mechanical harms, corrosion, erosion, damaged coatings, adverse operating condition, sea currents, and generally the relatively harsh subsea environment. In regard to corrosion, the external surface of the subsea object is generally exposed to potentially corrosive seawater, and the internal surface of the object (e.g., subsea piping and vessels) may be exposed to corrosive contents. Moreover, internal erosion may occur due to the flow of the contents through the subsea piping, pipeline, or vessels. Such erosion may be exacerbated by centrifugal forces associated with changes in the direction of the flow path. Significantly, erosion, corrosion, and other damage may cause gouges, cracks, stress corrosion cracking, and reduce the wall thickness of the subsea pipe or vessel, and thus reduce the pressure rating or pressure-holding capacity of the subsea pipe, pipeline, or vessel, as well as make subsea objects more susceptible to failure. Accordingly, operations and maintenance personnel of subsea objects (e.g., subsea piping, pipelines, vessels, risers, structures, etc.) may provide for inspection of the subsea objects, including in-place or in situ inspection and at a regular frequency. Such inspections of mechanical integrity may be related to or governed by applicable government or industry standards.

The inspection of subsea objects may involve visual inspection by a diver or inspection via hand-held devices by a diver, for example. However, the use of divers for subsea inspection may be problematic where the subsea objects are relatively deep and/or where and when strong sea currents exist. With regard to subsea pipelines, various techniques have been employed to detect defects, corrosion, and cracks in the pipelines. For example, pipeline inspection gauges or "pigs" may be pumped or pressured through the subsea pipeline to detect corrosion or cracks in the pipeline, and to measure thickness of the pipe wall. An intelligent or smart "pig" may include electronics and sensors that collect various forms of data during the trip through the pipeline. Modern intelligent pigs may be highly sophisticated instruments that vary in technology and complexity by the intended use and by manufacturer. However, valves and other components along the pipeline may give internal obstructions in the pipeline making use of a pig problematic.

SUMMARY

An embodiment provides an electromagnetic acoustic transducer for inspecting a subsea object. The electromagnetic acoustic transducer may comprise: a magnet to generate a magnetic field in a subsea object; a coil to induce eddy currents on a surface of the subsea object; sea water flow-through holes to funnel sea water adjacent the coil; and a substantially non-conductive wear plate disposed on a bottom portion of the electromagnetic acoustic transducer.

Another embodiment provides an electromagnetic acoustic transducer scanner assembly for inspecting a subsea object. The electromagnetic acoustic transducer scanner assembly may comprise: a carriage; a first transducer cart comprising an electromagnetic acoustic transducer transmitter; and a second transducer cart comprising an electromagnetic acoustic transducer receiver, wherein the first and second transducer carts are each disposed in the carriage and configured for use subsea inspection.

Another embodiment provides a method of operating a subsea electromagnetic acoustic transducer scanner assembly to inspect a subsea object, the method may comprise: deploying the electromagnetic acoustic transducer scanner assembly subsea; driving the electromagnetic acoustic transducer scanner assembly along the subsea object to be inspected; instructing remotely the electromagnetic acoustic transducer scanner assembly to inspect the subsea object; and collecting subsea inspection data of the subsea object via the electromagnetic acoustic transducer scanner assembly.

BRIEF DESCRIPTION OF THE DRAWINGS

These drawings illustrate certain aspects of some of the embodiments of the present invention, and should not be used to limit or define the invention.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill in the art and having the benefit of this disclosure. Although individual embodiments are discussed, the invention covers all combinations of all those embodiments. While compositions and methods are described in terms of "comprising," "containing," or "including" various components or steps, the compositions and methods can also "consist essentially of" or "consist of" the various components and steps.

The present techniques are directed to detecting defects, such as corrosion or cracks, in subsea objects (e.g., subsea tubular items, piping, pipelines, vessels, risers, structures, etc.) while the subsea objects remain in situ subsea. More particularly, the techniques relate to an EMAT system and method for detecting defects and/or wall thickness in subsea pipe work and risers commonly used in subsea drilling and production operations, as well as in more general subsea objects and applications. As discussed in more detail later in this disclosure, features that may be used in certain embodiment to advance subsea applicability may include one or more of (1) sea water flow through holes; (2) protective slide plates; (3) metal backing on the EMAT coil; and (4) non-conductive wear plate, or other features.

With regard to pipelines, a self-propelled EMAT scanner may be employed to travel along the axial length of the exterior surface of the subsea pipeline to inspect the pipeline for corrosion, cracks, stress corrosion cracking, pitting, pipe wall thickness, and defects generally. In general, the techniques may include an EMAT sensor, subsea deployment system, associated procedure, and software for the subsea inspection of metal objects including risers, structures, and tubular metals components including metal piping and pipelines. In this non-destructive inspection system and approach, the sensors may be enclosed in a protective casing attached to a magnet wheel scanner, which may be controlled by either a wireline and/or via remote operated vehicle (ROV) from the surface, for example. The casing or housing may protect the internal sensor components and reduce damage to the inspection system caused by the challenging environment on the subsea.

Such ultrasonic inspection may be employed as a non-destructive (NDE) technique for detecting corrosion and cracking in different objects such as metallic components, pipes, pipelines, risers, vessels, and so forth. Electromagnetic acoustic transducers (EMATs) are ultrasonic transducers that couple acoustic energy into and out of an object electromagnetically rather than necessarily through the use of an acoustic coupling medium, such as water or grease. Thus, electromagnetic acoustic transducers to be used in a variety of applications where the use of a particular coupling medium between the transducer and the specimen is either impractical or undesirable. Of course, in the instant subsea applications, sea water may provide a coupling medium.

An EMAT generates ultrasonic energy in an object by applying a magnetic field to the object using a magnet, and inducing electromagnetic eddy-currents (e.g., radio frequency RF eddy-currents) into the object using an electromagnetic coil (e.g., RF coil). The electromagnetic (e.g., RF) pulses interact with the magnetic field to produce a Lorentz force, for example, which in turn produces ultrasonic waves at the given frequency in the object. The strength of the generated force may depend on the proximity of the probe to the object. The EMAT may include the transducers and a carriage device, as well as be driven by a remote operated vehicle (ROV) and associated controls. A wear plate may be attached to the electromagnetic transducer to protect the magnets and the coil from wear due to the motion of the EMAT and contact with other components, such as the object being inspected.

Lastly, the described embodiments are generally directed toward an EMAT, which as mentioned may be used for non-destructive inspection applications. Such applications may include pipe inspection systems, pressure vessel inspection, riser or structural inspection, and so on, and generally provide for useful two-dimensional and three-dimensional data and context. To facilitate explanation, however, pipe (pipeline) inspection implementations will be generally discussed herein, though it is to be understood that other inspection implementations are also with the scope of the present techniques.

Figure 1:
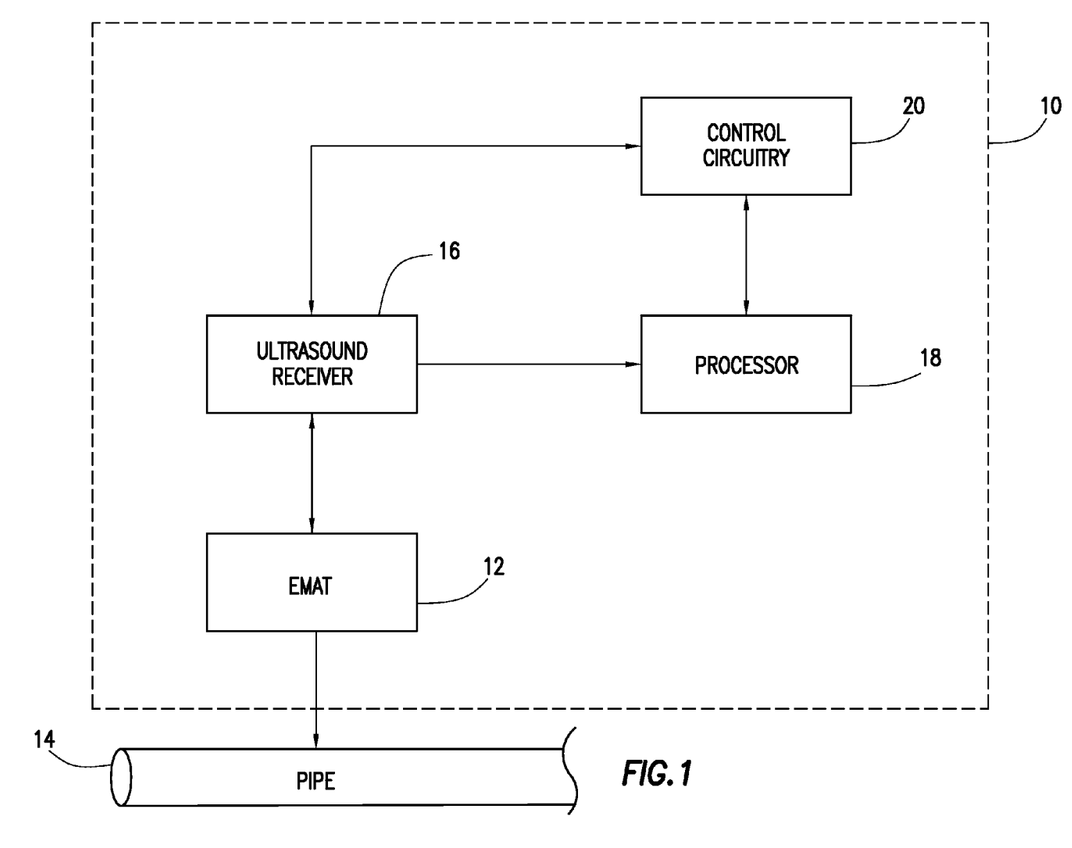
FIG. 1 illustrates an ultrasonic inspection system which implements an EMAT in accordance with embodiments of the present techniques.

Turning now to the drawings, FIG. 1 depicts an ultrasonic inspection system 10 which implements an EMAT 12 in conjunction with an ultrasound receiver system in accordance with embodiments of the present techniques. For the purpose of the description, the object is a pipe 14. The EMAT 12 may generate ultrasonic waves directly in the electrically conductive material via electromagnetic fields. Further, the EMAT 12 may receive acoustic signals representative of an area being inspected on the pipe 14. As discussed with regard to subsequent figures, the EMAT 12 may rest in a holder or carriage, tied to and moved via a remote operating vehicle (ROV), and beneficially includes, for example, sea water flow through holes, protective slide plates, a metal backing on the EMAT coil, a non-conductive wear plate, and/or the like.

Continuing with FIG. 1, the ultrasonic inspection system 10 further includes an ultrasound receiver 16 coupled to the EMAT 12. The ultrasound receiver 16 may be configured to receive the acoustic signals that are representative of the area of the object being inspected. The ultrasound receiver 16 may convert acoustic signals to electrical signals for further processing by the processor 18. The ultrasound receiver 16 may be further configured to excite electromagnetic components in the EMAT 12 by supplying frequency pulses. Exemplary pulses include spike pulses and square wave pulses. The frequency of the pulses may be set by control circuitry 20. The processor 18 may receive the electrical signals generated by the ultrasound receiver 16. The control circuitry 20 may further provide control signals indicative of the wave form characteristics (i.e., frequency, amplitude, and so forth) of the applied pulses to the processor 18. The processor 18 may apply various signal processing algorithms on the received data to generate required information, such as data indicative of the presence of defects, cracks, and so on, in the pipe being inspected. Various computing devices and unique software may be included for the control and management of the ultrasonic inspection system 10 and EMAT 12.

Figure 2:
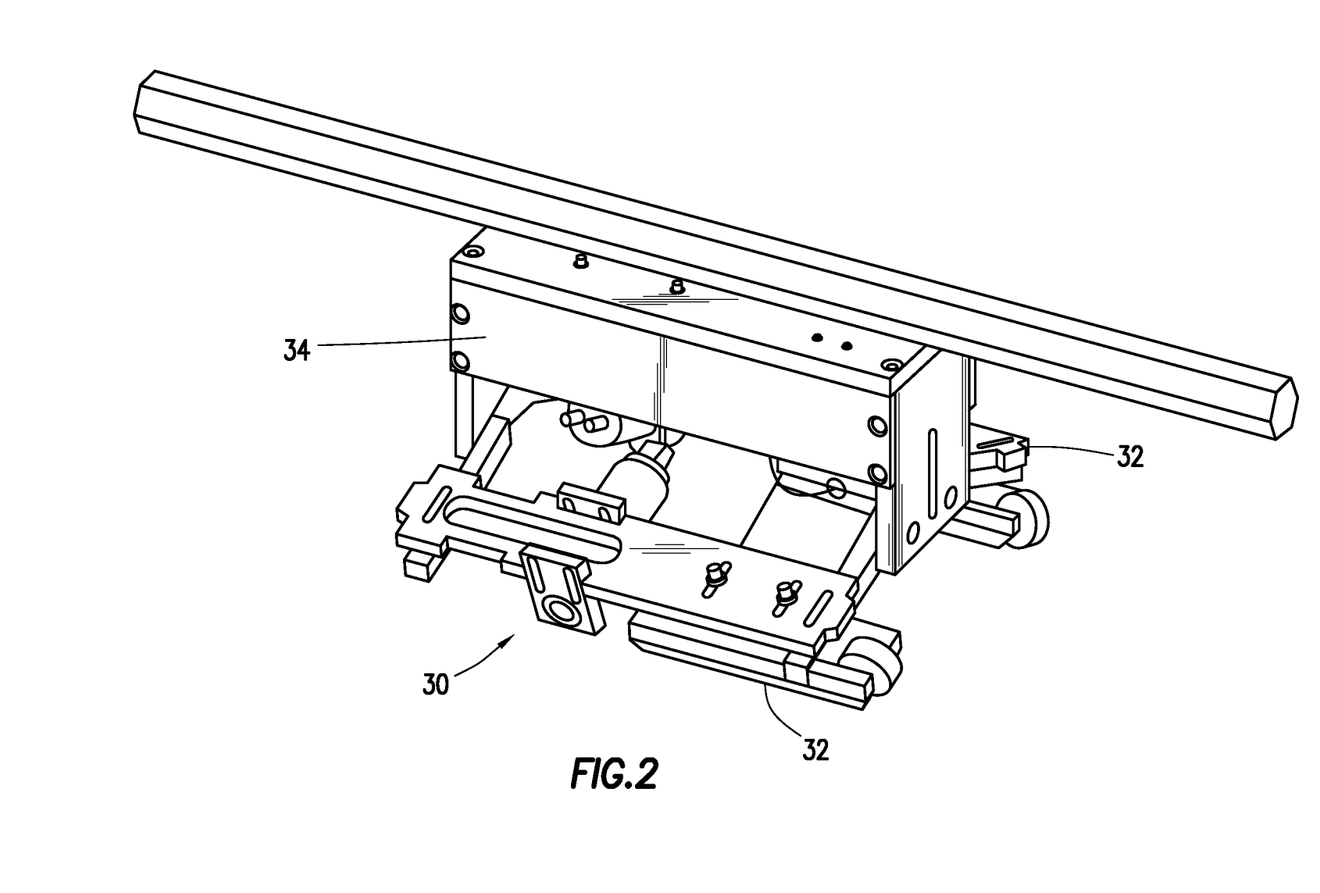
FIG. 2 illustrates an exemplary subsea EMAT scanner assembly in accordance with embodiments of the present techniques.

FIG. 2 is a view of an exemplary subsea EMAT scanner assembly 30 for subsea inspection of metallic objects (e.g., piping, pipelines) in accordance with embodiments of the present techniques. In the illustrated embodiment, the EMAT scanner assembly 30 has two EMAT transducer carts 32 which may be a respective EMAT transmitter and EMAT receiver. The EMAT scanner assembly 30 further includes a carriage 34 holding the two EMAT transducer carts 32. The EMAT transducer cart 32 is depicted in more detail in FIGS. 3 and 4. The EMAT scanner assembly 30 may include electronics and controls, be coupled to and driven by a ROV (e.g., a robotic device, a small submarine, etc.), i.e., be ROV deployable, and be coupled to a control and display computing device above water, such as on a ship. In certain embodiments, a hydraulic or electric motor provides motive force for the ROV and EMAT scanner assembly 30. In other embodiments, a diver may push the EMAT assembly along the object being inspected, in addition to or in lieu of the ROV. Further, the EMAT scanner assembly 30 and/or cart 32 may be partially or fully covered with a protective coating.

Figure 3:
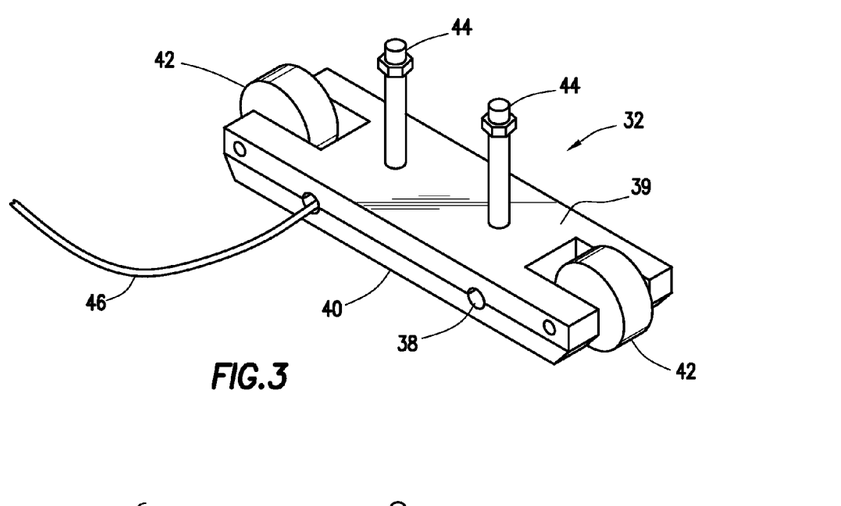
FIG. 3 illustrates an EMAT transducer cart in accordance with embodiments of the present techniques.
Figure 4A:
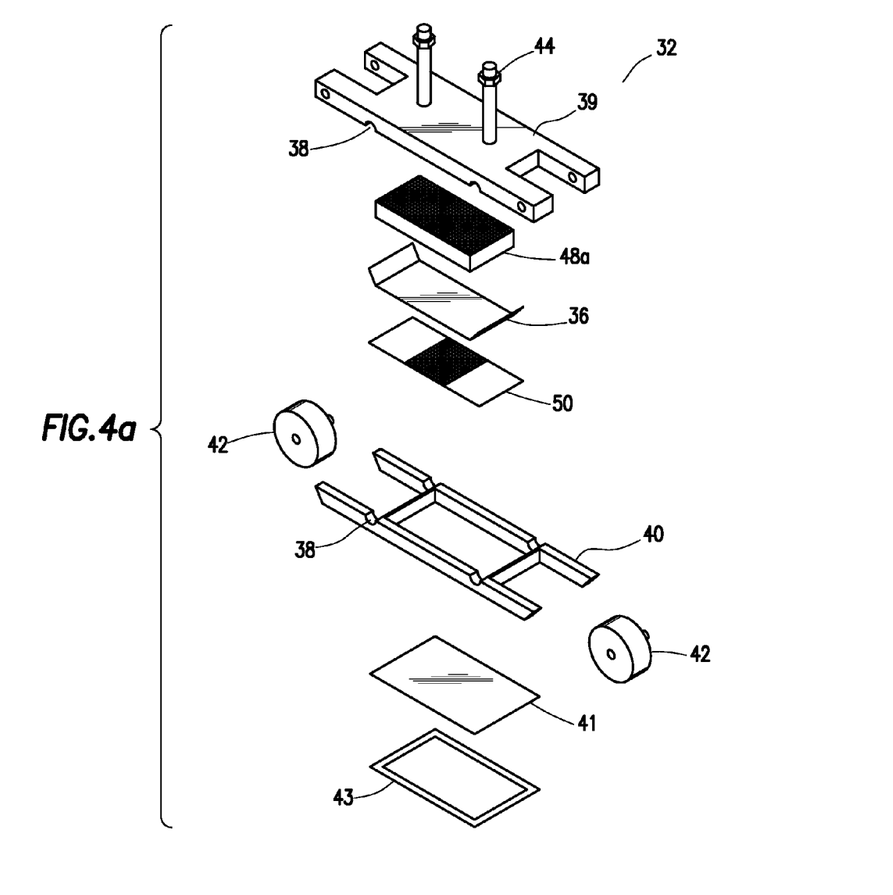
FIGS. 4a and 4b illustrate exploded views of exemplary EMAT transducer carts in accordance with embodiments of the present techniques.
Figure 4B:
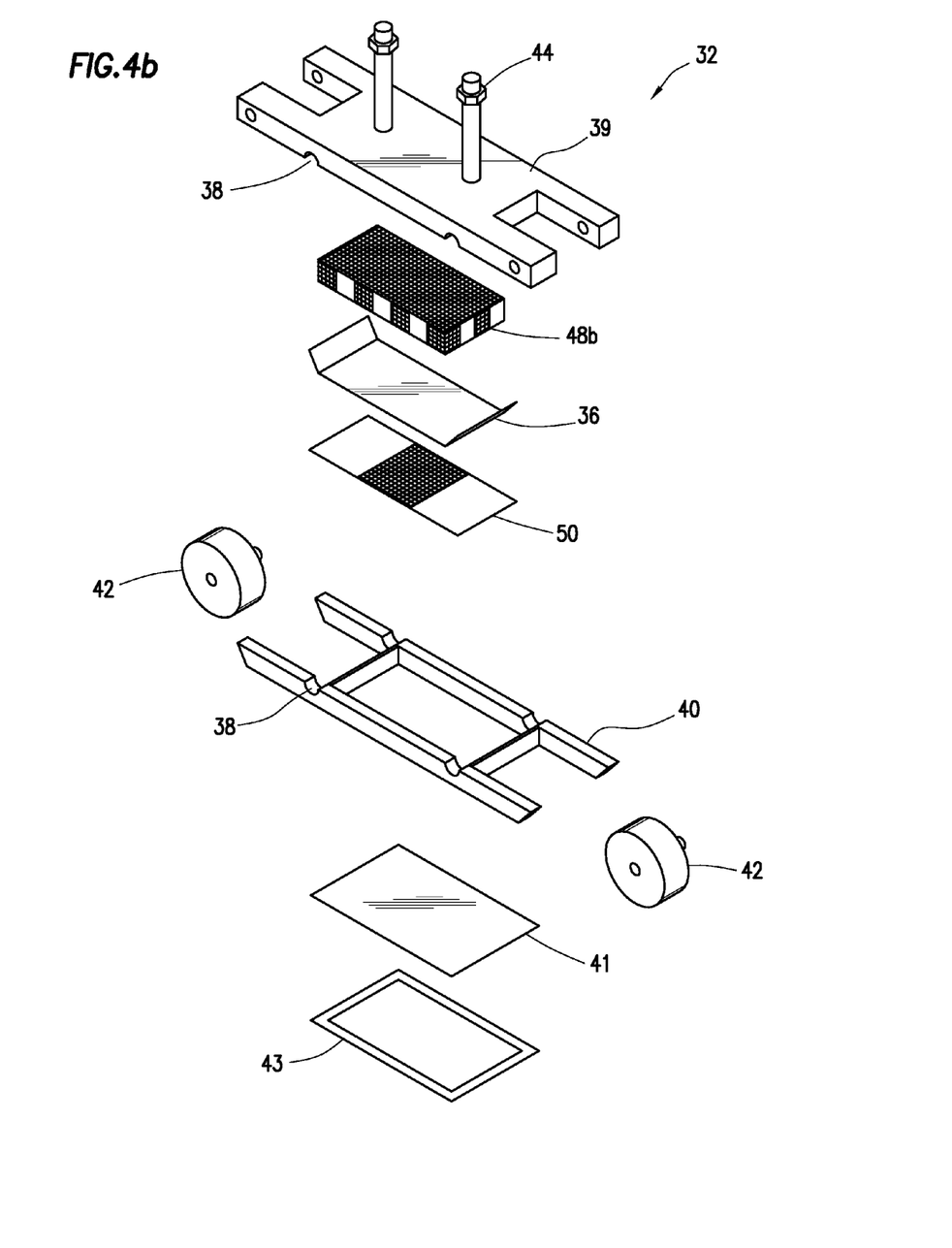

FIGS. 3, 4a, and 4b depict various views of the EMAT transducer cart 32 in accordance with embodiments of the present techniques. FIG. 4 is an exploded view of an embodiment of the transducer cart 32. As illustrated, the transducer cart 32 may include: a metal (e.g., copper) shielding 36 behind the EMAT coil 50; sea water flow through holes 38 that facilitate electrical conductivity and electrical ground scheme; and protector slide plates 40 which protect the EMAT coil 50 from irregularities on the object (e.g., pipe or pipeline) surface including welds and sea growth. The cart 32 may include a non-conductive wear plate 41 disposed on the bottom of the cart 32. The EMAT transducer cart 32 may include front and rear wheels 42 to facilitate movement of the cart 32 (and EMAT scanner assembly 30 shown on FIG. 2, for example) along the object being inspected. The EMAT transducer cart 32 may includes connectors 44 (e.g., attachment bolts and fittings) to help secure the cart 32 to the carriage 34 (e.g., shown on FIG. 2). Further, the cart 32 may include or be coupled to a control cable or wiring 46 to provide communication with control point or computing device above water. In one example, the control cable 46 is fiber optic and may be one to two miles in length. In alternative embodiments, the control cable or wiring 46 may provide communication with EMAT electronics coupled to an ROV. The cart 32 may further include a body portion 39. As illustrated, the body portion 39 may form an upper surface and upper sidewalls of the cart 32. In some embodiments, the body portion 39 may be steel and form a backing for attachment of the other components of the cart 32.

With specific reference to FIGS. 4a and 4b, an exploded view of the EMAT transducer cart 32 is shown having a magnetic component, which may be a magnet 48a (FIG. 4a) or a periodic permanent magnetic array 48b (FIG. 4b) for shear wave (SH) transducers. The transducer cart also includes an EMAT coil 50 in accordance with embodiments of the present techniques. In the embodiment illustrated in FIG. 4a, the magnet 48 may be about 2 inches long, 2 inches wide, and 0.5 inches in height. The magnet 48a (or period permanent magnetic array 48b) may be disposed in a middle portion of the cart 32. The EMAT transducer cart 32 may be an EMAT transmitter or an EMAT receiver in the assembly 30. In certain configurations, the transducers with the cart 32 may be disposed toward the front of the assembly 30, and a hydraulic motive force disposed toward the rear of the assembly, for instance. Further, electronics disposed on the carriage or ROV may be coupled to the cart 32. Moreover, the assembly 30 or ROV may optionally have a camera to capture images of the object being inspected.

The sea water flow-through holes 38 may function to facilitate sea water to surround the EMAT coil 50 to promote electrical grounding of the EMAT coil via the conductive sea water and, therefore, facilitate use of the substantially non-conductive (non-metallic) wear plate 41 on the front surface of the EMAT coil 50. In other words, instead of relying on conductivity of a metal (e.g., titanium) wear plate to shield the EMAT coil from electronic background interference, the sea water via the sea water flow-through holes 38 provides the electronic conductivity to shield the EMAT coil 50. To further explain, the EMAT coil 50 is sensitive to changes in the electronic field and may be affected by external interference such as radar and other background noise including radio noise. In the illustrated embodiment, the sea water flow-through holes are formed in the body portion 39 and the slide protective cover 40.

The non-metallic wear plate 41 may be used to protect the EMAT coils 50 which are generally fragile. Exemplary materials for the plate 41 may include aluminum oxide, polyethylene terephthalate (PET), and other non-metallic materials. The negligible conductivity of the non-metallic wear plate 41 should not reduce the amplitude of the signal generated in the object (pipe) being inspected, and therefore advantageously may increase the signal-to-noise ratio of the EMAT coil 50. Indeed, as a result, more signal may be introduced into the object (pipe) being inspected. As illustrated, a wear plate cover 43 may be disposed on a lower side of the wear plate 41. In some embodiments, the wear plate cover 43 may be analogous in shape to a window or picture frame or other geometer.

In the illustrated embodiment, the slide protector cover 40 (e.g., protective slide plates) run along substantially the full length of the EMAT transducer cart 32, and along the front and back edge of the EMAT coil 50. Of course, a slide protector cover 40 covering or running along less of the cart 32 may be employed. The slide protector cover 40 generally may function to scrape off and or lift the EMAT cart 32 (and assembly 30, shown on FIG. 2, for example) over marine growth on the pipe and also may facilitate the EMAT transducer cart 32 to slide over circumferential welds on the pipe. The slide protector cover 40 may be analogous in shape to a window or picture frame or other geometry.

Further, the metal (e.g., copper) backing (reflective plate) 36 adjacent the EMAT coil (i.e., between the magnetic component and EMAT coil 50) may advantageously reflect the eddy currents produced by the EMAT coil 50 and reduce ultrasound from being generated in the backing magnet or backing material. Beneficially, this may increase the signal-to-noise ration of the EMAT sensor.

Figure 5:
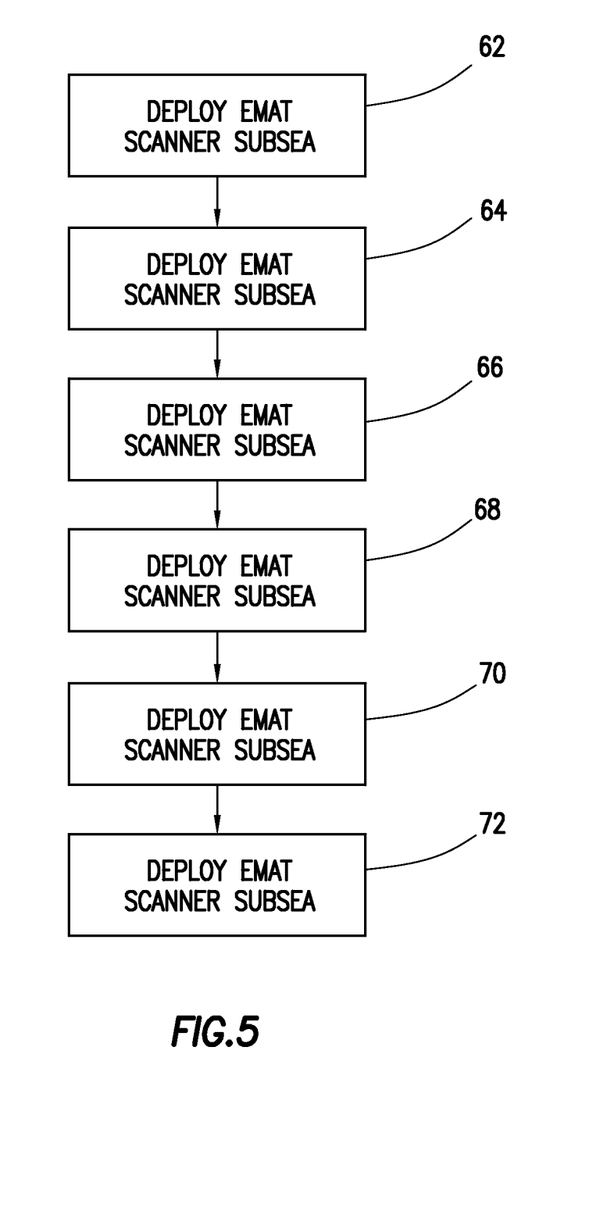
FIG. 5 illustrates an exemplary method for employing an EMAT scanner assembly to inspect a subsea objection in accordance with embodiments of the present techniques.

FIG. 5 is a block diagram of an exemplary method 60 for employing the subsea EMAT scanner assembly 30 to inspect a subsea object in accordance with embodiments of the present techniques. Initially, the EMAT scanner assembly 30 is deployed (block 62) subsea and then driven (block 64) along the subsea object being inspected in-situ. The EMAT scanner 60 may be instructed (block 66) and communicated with (and controlled) via an above-water operator and computing device. The instructions given to the EMAT scanner assembly 30 (and ROV) may be with regard to the data to be collected and with respect to movement of the EMAT scanner assembly 30 including control of the ROV, and so forth. Special software may be employed on the above-water computing device and with respect to the subsea electronics associated with the EMAT scanner assembly 30 and ROV.

The EMAT scanner assembly 30 inspects (block 68) the subsea object or a portion of the subsea object. During the inspection, sea water may flow through sea water flow-through holes of the scanner assembly 30 to promote a better signal-to-noise ratio in the subsea object. The above-ground computing device and/or electronics coupled to the scanner assembly 30 in the subsea may collect (block 70) and store movement and inspection data. Lastly, upon completion of the subsea object or a portion of the subsea object, the EMAT scanner assembly 30 may be removed (block 72) from the subsea environment to above-water such as to a ship, platform, ground, etc.

Figure 6:
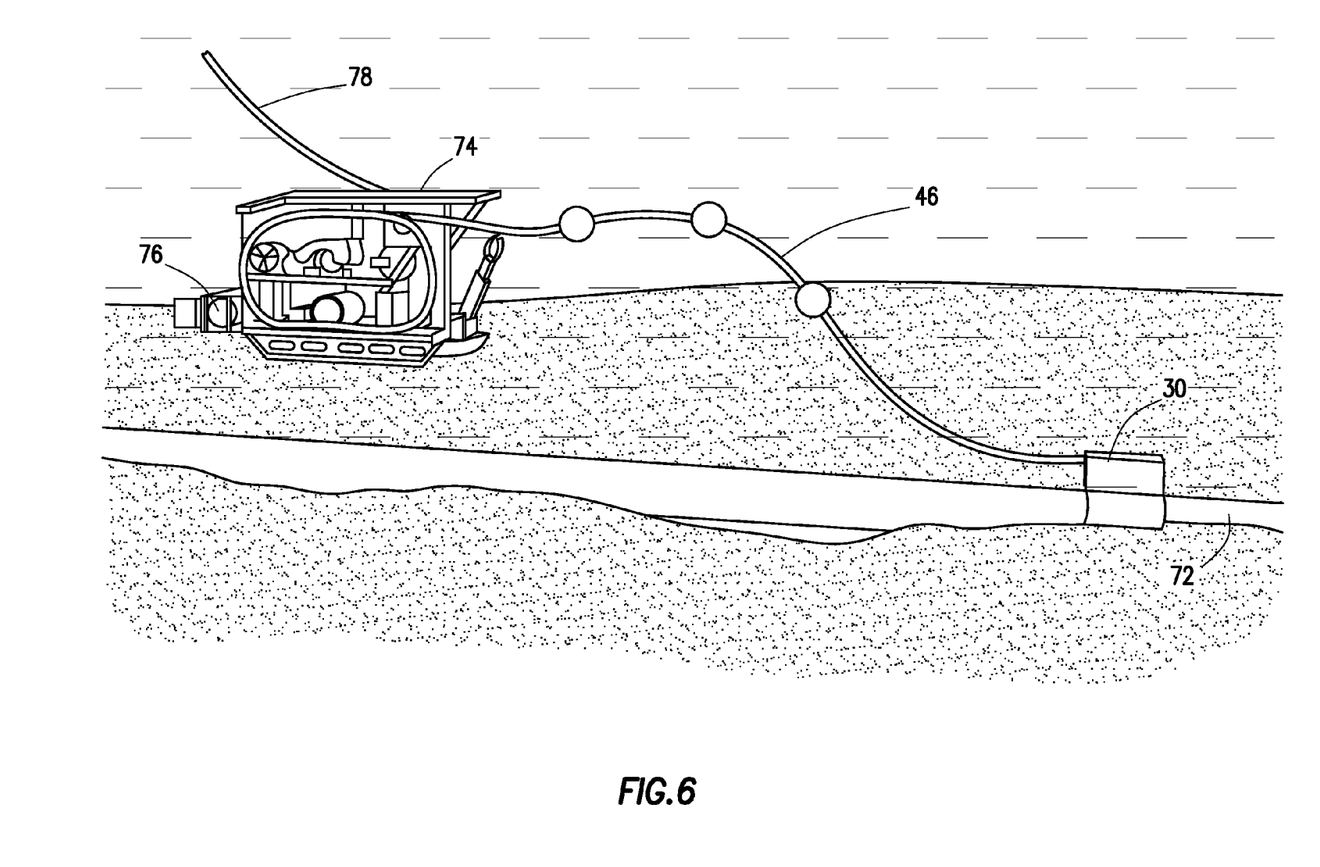
FIGS. 6 and 7 illustrate an exemplary subsea scanner assembly deployed from a remote operated vehicle for inspection of a subsea object in accordance with embodiments of the present techniques.
Figure 7:
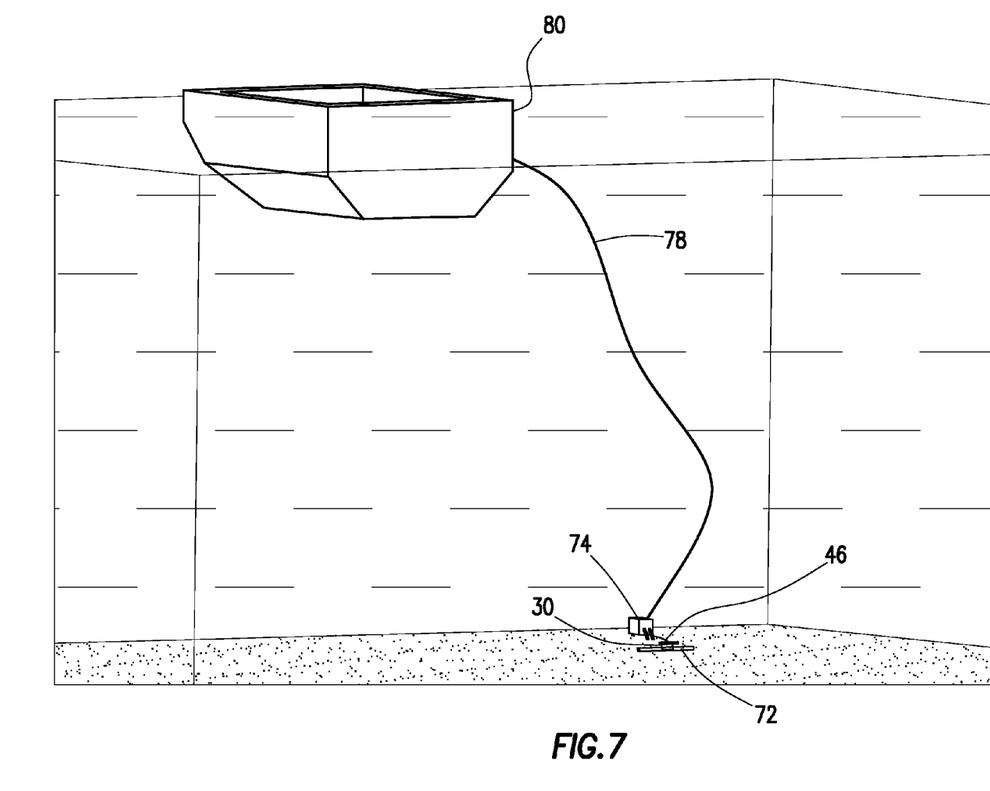

FIGS. 6 and 7 illustrate use of an exemplary subsea EMAT scanner in inspection of a subsea object 72 in accordance with embodiments of the present technique. As illustrated, an ROV 74 may be used to place the EMAT scanner assembly 30 onto the subsea objection 72. The EMAT scanner assembly 30 may be coupled to the ROV 74 by a control cable 46, for example. An EMAT electronics enclosure 76 may be coupled to the ROV 74. The electronics enclosure 76 may contain electronics for controlling the scanner assembly 30, such as the processor 18 and the control circuitry 20 shown on FIG. 1, for example. The control cable 46 may provide communication between the scanner assembly 30 and the electronics enclosure 76 and/or the ROV 74. The ROV 74 may provide control signals, electrical power, and/or hydraulic power to the electronics enclosure 76 and the scanner assembly 30. Additionally, the ROV 74 may provide motive force for pushing the scanner assembly 30 along the axial length of the subsea object 72. In accordance with present embodiments, the scanner assembly 30 may perform an inspection of the subsea object 72 as it is moved along the axial length of the subsea object 72. As illustrated, a second control cable 78 may extend between the ROV 74 and a vessel 80 at the water's surface, for example. The second control cable 78 may be fiber optic and may be one to two miles in length, for example. The second control cable 78 may provide communication between the scanner assembly 30 and a computing device on the vessel 80, for example. In some embodiments, an operator on the vessel 80 may control the real-time inspection of the subsea object 72.

Figure 8:
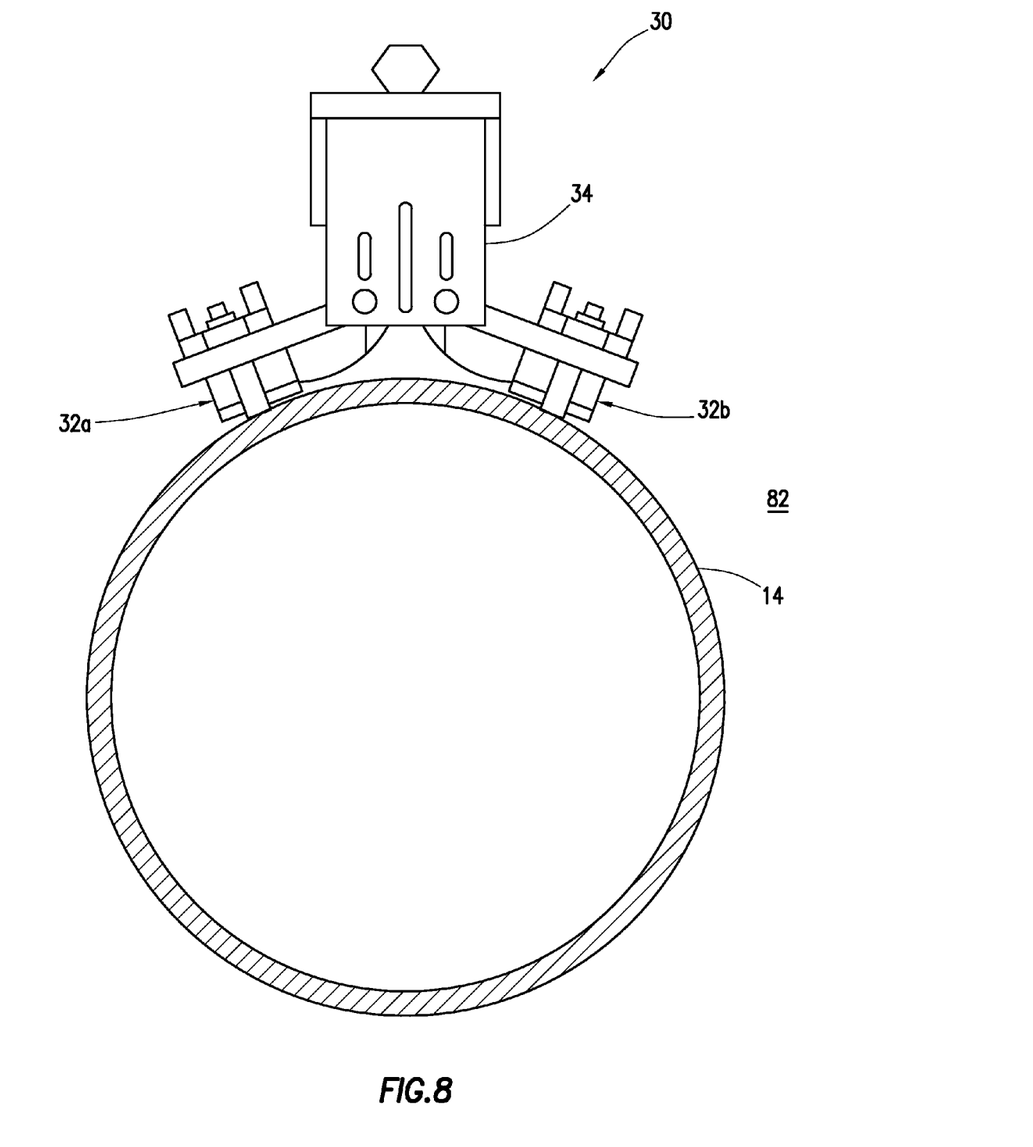
FIG. 8 illustrates an exemplary EMAT scanner assembly inspecting a subsea object in accordance with embodiments of the present techniques.

FIG. 8 illustrates an EMAT scanner assembly 30 disposed on a pipe 14 disposed in water 82. As illustrated, the scanner assembly 30 may include a carriage 34 and EMAT transducer carts, shown as first EMAT transducer cart 32a and second EMAT transducer cart 32b. As previously described, the EMAT scanner assembly 30 may be used to generate ultrasonic waves in the pipe 14. In particular embodiments, the first EMAT transducer cart 32a may include an EMAT transducer transmitter (not shown) and the second EMAT transducer cart may include an EMAT transducer receiver (not shown). By way of example, the EMAT transducer transmitter may induce ultrasonic waves in the pipe 14 which may be detected by the EMAT transducer receiver. A signal pattern may be detected in which two signals appear, namely a first signal that that traveled counterclockwise around the pipe 14 and a second signal that traveled clockwise around the pipe 14. However, because the scanner assembly 30 is disposed in the water 82, ultrasonic waves are also induced in the water 82. The ultrasonic waves induced in the water 82 travel directly between the EMAT transducer transmitter and the EMAT transducer receiver, resulting in a standing wave in the detected signals that negatively impacts the inspection.

A number of different techniques may be used to reduce and/or eliminate the deleterious effects of the standing wave on the subsea inspection. An example of such a technique utilizes shear horizontal waves. For example, shear horizontal wave transducers may be incorporated into the scanner assembly 30 such that the scanner assembly induces shear horizontal waves in the pipe 14 or other subsea object. Because the shear horizontal waves are polarized in the horizontal plane they should not transmit through the water 82, for example, between the EMAT transducer carts 32. Another example of a technique for reducing or eliminating the standing wave may utilize optimized Lamb waves. For example, the scanner assembly 30 may be configured to induce optimized Lamb waves in the pipe 14 or other subsea object. In particular, the Lamb waves may be optimized with large tangential displacements and small normal displacements to decrease the percentage of ultrasonic waves induced in the water 82 while increasing the percentage of ultrasonic waves induced in the pipe 14 or other subsea object. In some embodiments, optimized Lamb waves may be used in which 70% or more of the ultrasonic waves are tangential. In further embodiments, optimized Lamb waves may be used in which 90% or more of the ultrasonic waves are tangential.

Figure 9:
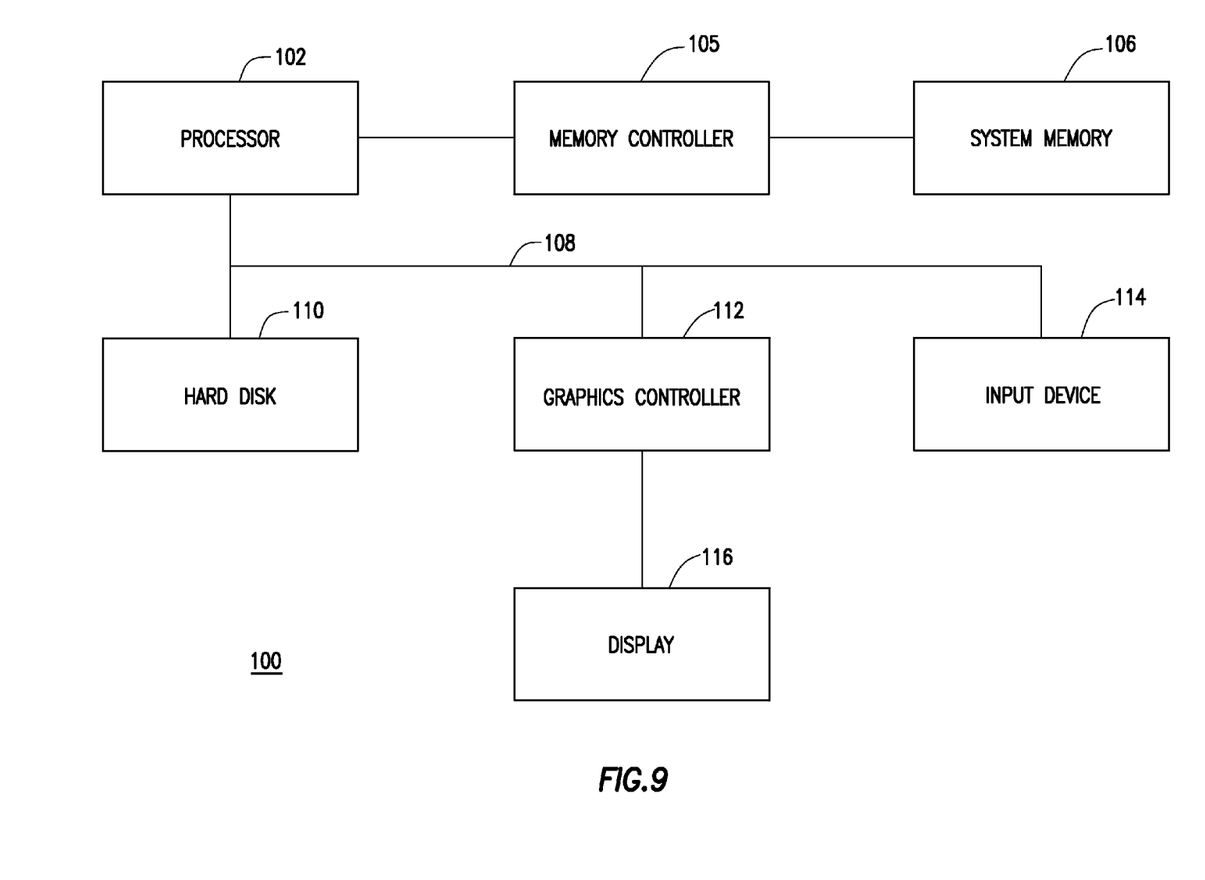
FIG. 9 illustrates an exemplary computer system that may be used in accordance with embodiments of the present techniques.

FIG. 10 is a block diagram of an exemplary computer system 100 that that may be used above-water to instruct and control a subsea EMAT scanner assembly. Special or unique software for operating the EMAT scanner assembly may be stored in the computer system and/or on external computer readable media. Those of ordinary skill in the art will appreciate that the computer system 100 may comprise hardware elements including circuitry, software elements including computer code stored on a machine-readable medium or a combination of both hardware and software elements. Additionally, the blocks shown are but one example of blocks that may be implemented. A processor 102, such as a central processing unit or CPU, controls the overall operation of the computer system 100. The processor 102 is connected to a memory controller 104, which reads data to and writes data from a system memory 106. The memory controller 104 may have memory that includes a non-volatile memory region and a volatile memory region. The system memory 106 may be composed of a plurality of memory modules, as will be appreciated by one of ordinary skill in the art. In addition, the system memory 106 may include non-volatile and volatile portions. A system basic input-output system (BIOS) may be stored in a non-volatile portion of the system memory 106. The system BIOS is adapted to control a start-up or boot process and to control the low-level operation of the computer system 100.

The processor 102 is connected to at least one system bus 108 to allow communication between the processor 102 and other system devices. The system bus may operate under a standard protocol such as a variation of the Peripheral Component Interconnect (PCI) bus or the like. In the exemplary embodiment shown in FIG. 10, the system bus 108 connects the processor 102 to a hard disk drive 110, a graphics controller 112 and at least one input device 114. The hard disk drive 110 provides non-volatile storage to data that is used by the computer system. The graphics controller 112 is in turn connected to a display device 116, which provides an image to a user based on activities performed by the computer system 100. The computer system 100 may be programmed to perform operation and control of a subsea EMAT scanner assembly, including with regard to movement and data collection, and the like. The memory devices of the computer system 100, including the system memory 106 and the hard disk 110 may be tangible, machine-readable media that store computer-readable instructions to cause the processor 102 to perform a method according to an embodiment of the present techniques.

The foregoing figures and discussion are not intended to include all features of the present techniques to accommodate a buyer or seller, or to describe the system, nor is such figures and discussion limiting but exemplary and in the spirit of the present techniques.

What is claimed is:

1. An electromagnetic acoustic transducer for inspecting a subsea object, comprising:
    a magnetic component to generate a magnetic field in a subsea object;
    a coil to induce eddy currents on a surface of the subsea object;
    sea water flow-through holes to funnel sea water adjacent the coil; and
    a substantially non-conductive wear plate, wherein the non-conductive wear plate comprises a non-metallic material, disposed on a bottom portion of the electromagnetic acoustic transducer.

2. The electromagnetic acoustic transducer of claim 1, comprising protective slide plates disposed on a bottom portion of the electromagnetic acoustic transducer.

3. The electromagnetic acoustic transducer of claim 1, comprising a metal backing on the coil.

4. The electromagnetic acoustic transducer of claim 3, wherein the metal backing comprises a copper backing.

5. The electromagnetic acoustic transducer of claim 1, comprising a cart housing the electromagnetic acoustic transducer.

6. The electromagnetic acoustic transducer of claim 1, wherein the electromagnetic acoustic transducer is disposed in a carriage.

7. The electromagnetic acoustic transducer of claim 1, wherein the electromagnetic acoustic transducer is a shear horizontal wave transducer.

8. The electromagnetic acoustic transducer of claim 1, wherein the electromagnetic acoustic transducer is configured to induce Lamb waves in the subsea object, the Lamb waves being optimized such that 70% of more of the Lamb waves are tangential.

9. The electromagnetic acoustic transducer of claim 8, wherein 90% or more of the Lamb waves are tangential.

10. An electromagnetic acoustic transducer scanner assembly for inspecting a subsea object, comprising:
    a carriage;
    a control cable or tether to provide communication with a control point above water or a remote operated vehicle;
    a first transducer cart comprising an electromagnetic acoustic transducer transmitter wherein the electromagnetic acoustic transducer transmitter comprises a magnet, electromagnetic acoustic transducer coil, sea water flow-through holes to funnel sea water adjacent the coil, and a non-metallic wear plate; and
    a second transducer cart comprising an electromagnetic acoustic transducer receiver, wherein the electromagnetic acoustic transducer receiver comprises a magnet, electromagnetic acoustic transducer coil, sea water flow-through holes to funnel sea water adjacent the coil, and a non-metallic wear plate, wherein the first and second transducer carts are each disposed in the carriage and configured for use in subsea inspection.

11. The electromagnetic acoustic transducer scanner assembly of claim 10, comprising protective slide plates on the first and second transducer carts.

12. The electromagnetic acoustic transducer scanner assembly of claim 10, comprising a metal backing on each coil.

13. The electromagnetic acoustic transducer scanner assembly of claim 12, wherein the metal backing comprises a copper backing.

14. The electromagnetic acoustic transducer scanner assembly of claim 10, wherein the electromagnetic acoustic transducer transmitter is a shear horizontal wave transducer.

15. The electromagnetic acoustic transducer of claim 10, wherein the electromagnetic acoustic transducer transmitter is configured to induce Lamb waves in the subsea object, the Lamb waves being optimized such that 70% of more of the Lamb waves are tangential.

16. A method of operating a subsea electromagnetic acoustic transducer scanner assembly to inspect a subsea object, the method comprising:
    deploying the electromagnetic acoustic transducer scanner assembly subsea, wherein the electromagnetic acoustic transducer scanner assembly comprises a first transducer cart comprising an electromagnetic acoustic transducer transmitter, wherein the electromagnetic acoustic transducer transmitter comprises a magnet, electromagnetic acoustic transducer coil, sea water flow-through holes to funnel sea water adjacent the coil, and a non-metallic wear plate, and a second transducer cart comprising an electromagnetic acoustic transducer receiver, wherein the electromagnetic acoustic transducer receiver comprises a magnet, electromagnetic acoustic transducer coil, sea water flow-through holes to funnel sea water adjacent the coil, and a non-metallic wear plate;
    driving the electromagnetic acoustic transducer scanner assembly along the subsea object to be inspected;
    instructing remotely the electromagnetic acoustic transducer scanner assembly to inspect the subsea object;
    surrounding the coils with seawater to promote electrical grounding, wherein the seawater entering through the flow-through holes shields the coils from background interference;
    collecting subsea inspection data of the subsea object via the electromagnetic acoustic transducer scanner assembly; and
    communicating the data to the surface of the water.

17. The method of claim 16, comprising routing seawater adjacent a sensor of the electromagnetic acoustic transducer scanner assembly.

18. The method of claim 16, wherein the deploying the electromagnetic acoustic transducer scanner assembly comprises using a remote operated vehicle.

* * * * *